United States Patent

Ober et al.

[11] 4,038,706
[45] Aug. 2, 1977

[54] ARTIFICIAL ELBOW MECHANISM

[75] Inventors: Jan Ober; Zygmunt Piatek, both of Poznan, Poland

[73] Assignee: Centralnt Osrodek Techniki Medycznej, Warsaw, Poland

[21] Appl. No.: 641,087

[22] Filed: Dec. 15, 1975

[30] Foreign Application Priority Data

Dec. 20, 1974 Poland .................................. 176647

[51] Int. Cl.² ................................................ A61F 1/06
[52] U.S. Cl. .................................................... 3/12.3
[58] Field of Search ................................ 3/12–12.8, 3/21

[56] References Cited

U.S. PATENT DOCUMENTS

| 767,201 | 8/1904 | Bennett | 3/12.2 |
| 1,272,179 | 7/1918 | Anderson et al. | 3/12.3 |
| 1,273,461 | 7/1918 | Corley | 3/12.3 |
| 3,526,007 | 9/1970 | Ivko et al. | 3/12.1 |
| 3,833,942 | 9/1974 | Collins | 3/12.3 |

FOREIGN PATENT DOCUMENTS

| 486,305 | 12/1917 | France | 3/12.2 |

Primary Examiner—Ronald L. Frinks

[57] ABSTRACT

Artificial elbow mechanism featured with the bending and active locking mechanisms attached to one control cable in such a way that the control cable passes on a pulley in the forearm part creating the point of application of a forearm flexion force and subsequently on a pulley accommodated inside the lock being the point of application of a force for releasing the lock by pulling the lock out from a cut-out in the arm part.

6 Claims, 10 Drawing Figures

ARTIFICIAL ELBOW MECHANISM

FIELD OF THE INVENTION

The present invention relates to an artificial elbow mechanism designed for a body powered upper limb prosthesis.

BACKGROUND OF THE INVENTION

Elbow mechanisms heretofore known are provided with a latch locking mechanism placed in the arm portion of the mechanism. The locking mechanism is controlled by means of one control cable, the elbow flexion motion being effected by a control cable.

The aforementioned mechanism has many drawbacks and disadvantages. It requires two control movements from two separate units of the control harness. So, for instance, flexion of the elbow followed with locking in a chosen flexion position requires the following motions: unlocking the mechanism by pulling the control cable, flexion of the forearm by pulling a separate cable, and locking the mechanism by pulling again the locking cable. This control means is hard for a patient to master and at the same time it's execution was very troublesome. Another drawback consists in that the locking mechanism is located in the arm portion of the elbow and consequently cannot be used in the case of long arm stumps, eg., in the case of elbow disarticulation. Moreover, its range of application is also limited to a determined elbow size, this being different in case of children and adults. What is more, this mechanism can only be used either for a body powered arm or for a cosmetic passive limb coated with a body-like soft cover that is either for a prosthesis made with the use of extraskeletal or intraskeletal technique. Mechanical design heretofore used is both complicated and expensive.

SUMMARY OF THE INVENTION

The essential idea of the elbow mechanism according to the present invention consists in that the flexion and active locking mechanisms are connected to one control cable in such a way that the control cable passes on a pulley in the forearm part, being the point of flexion force application, and then on the second pulley, being the point of application of a force pulling the lock from a cut-out in the arm portion. The active locking mechanism is situated in the forearm portion.

Another feature of the present invention is that a cable shortening mechanism possessing a disc with journals is mounted on skeleton rods in the forearm part in a plane perpendicular to the latter, on which a revolving spring lever is mounted, whereas the control cable going out from the forearm portion of the elbow passes through an opening in the disc and then through an eyelet in a lever catch and finally is fixed onto the disc. The artificial elbow mechanism is fitted with a connecting link in the shape of a cylinder, revolving disc or mounting plate to be connected either with an arm made with the use of extraskeletal or intraskeletal technique or finally, with an arm socket in the case of elbow disarticulation.

The elbow mechanism according to the invention has several advantages. Owing to the application of only one control cable and consequently only one control movement, the elbow operation by the patient has been considerably facilitated. The remaining unutilized control movement of a control harness (usually the movement of the neck straightening) can be used for controlling the other mechanism of the arm prosthesis, for instance, for the forearm rotation. Owing to the location of the locking mechanism in the forearm portion and fitting it with a cable shortening mechanism and, in consequence, a simple and compact design of small dimensions, it has been possible to extend the range of application of the elbow mechanism it can now be used also for a body powered arm prostheses with an active flexion end locking of the elbow as well as for cosmetic prostheses with a passive locking elbow controlled from the forearm these artificial limbs can be according to extraskeletal as well as to intraskeleton techniques, together with the disarticulation in the elbow joint. A mechanism of only one size can be used both for adults and children. The mechanism according to the invention may also be used as an elbow joint of armorthosis.

BRIEF DESCRIPTION OF DRAWING

The artificial elbow mechanism according to the invention is presented in an exemplary embodiment as illustrated in the accompanying drawing in which.

DETAILED DESCRIPTION

Figure 1:
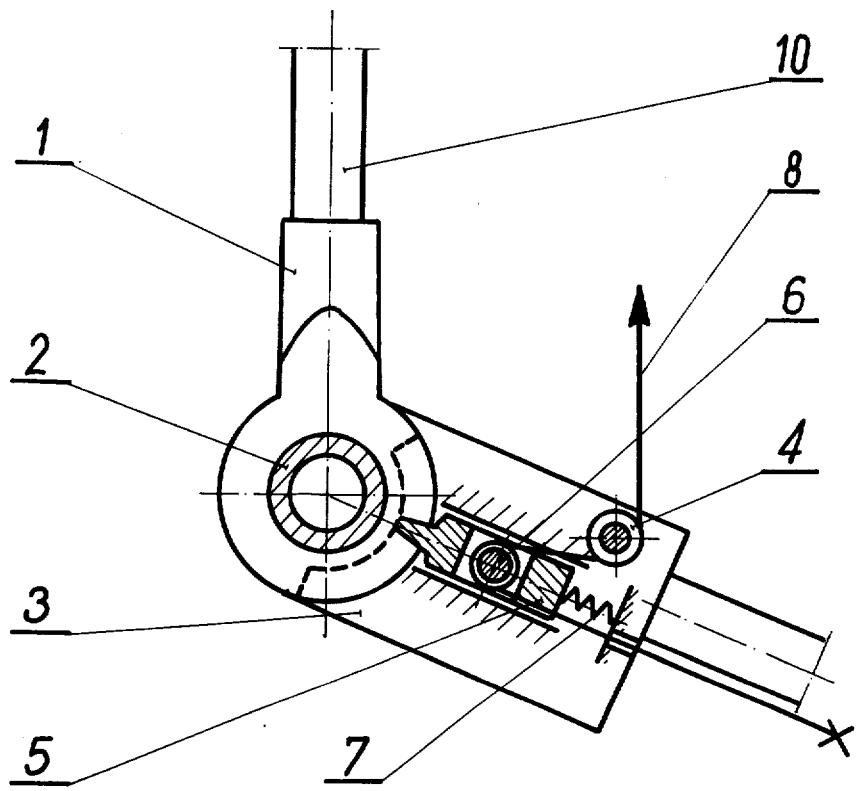
FIG. 1 is a diagram of the mechanism in longitudinal section.

The elbow mechanism according to the present invention consists of arm part 1 connected by means of shaft 2 with a revolving forearm part 3. The arm part 1 is made in the form of a disc with cut-outs over part of the circumference of the disc equal to the range of the flexion movement of the elbow mechanism. The forearm part is made in the form of a body accommodating a stationary pulley 4 and a slidable lock 5. Inside this lock there is a pulley 6. The front part of the lock 5 enters into the cut-outs in the disc of the arm part 1.

Figure 2:
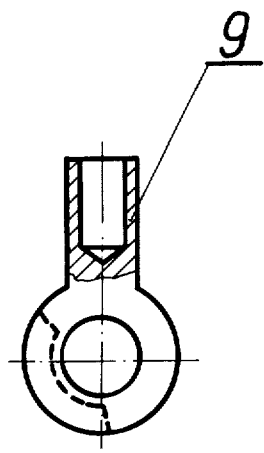
FIG. 2 is the arm part of the mechanism with a seat for cementing the artificial elbow
Figure 4:
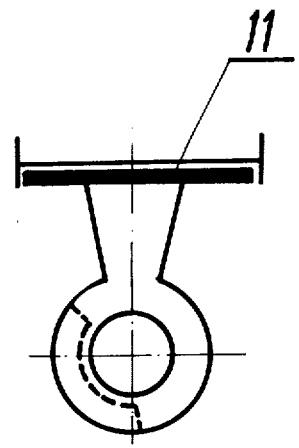
FIG. 4 shows the arm part of a mechanism with the revolving disc for mounting directly on the stump socket.
Figure 3:
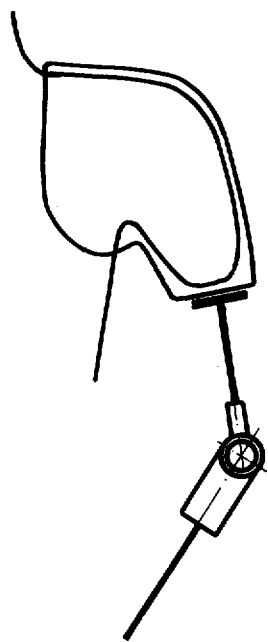
FIG. 3 shows an example of an application of an elbow mechanism with an arm part according to FIG. 2 in which a prosthesis for a short arm stump is made in an intraskeletal technique.
Figure 5:
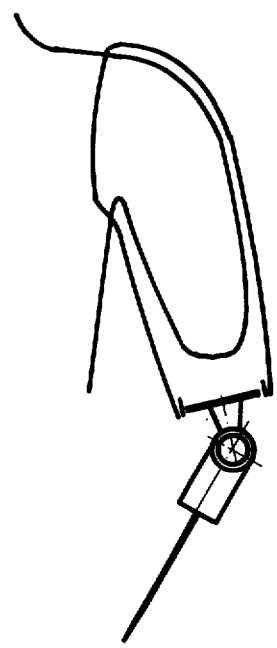
FIG. 5 is presented an example of the use of the presented mechanism with an arm part made according to FIG. 4 in the case of a long arm stump, when it is possible to make the entire arm part of the prosthesis in the extraskeletal technique.
Figure 6:
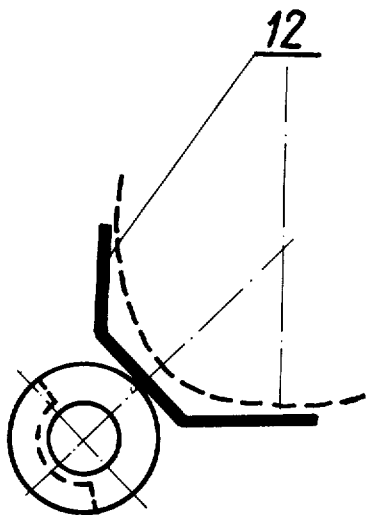
FIG. 6 shows an arm part of the mechanism with an angular connecting link to be mounted directly on the stump socket.
Figure 7:
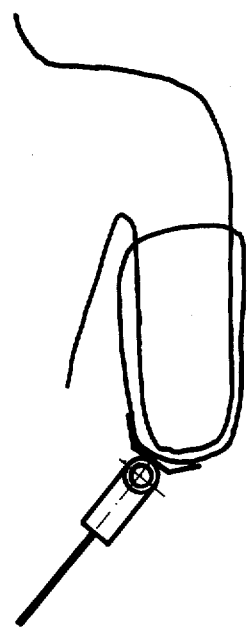
FIG. 7 is an example of application of the mechanism with the arm part according to FIG. 6 in a case of elbow disarticulation.

Between the front part of the lock 5 and the body 3 there is a return spring 7 of the lock 5. One end of the control cable 8 is connected to the output of a control harness (not shown in the drawing) located on the patient's body, and passes on pulleys 4 and 6. The second end of control cable 8 is attached to the body 3 or cable 8 may go out of body 3 and can be externally attached, for example to the cable shortening mechanism. The end of the control cable 8 going out from the body 3 can also be connected to a system of microswitches for controlling the function of an electric hand. The arm part 1 visible in FIG. 2 is completed by a joint 9 in the shape of a cylinder with a center bore accommodating a supporting rod 10 of the skeleton of the prosthesis. In FIG. 4 is presented another embodiment of the arm part 1, in which a connecting link is fitted with a revolving disc 11 rendering it possible for the mechanism to be connected to the stump socket. In FIG. 6 is shown still another embodiment of the arm part 1, which is terminated with a mounting plate in the shape of an angular connecting link 12 rendering it possible for the elbow mechanism to be attached directly to the stump and thus insuring a minimum distance between the axis of elbow rotation and the stump end. FIGS. 3, 5 and 7 present various application of the mechanism with the arm parts presented in FIGS. 2, 4 and 6, respectively.

Figure 8:
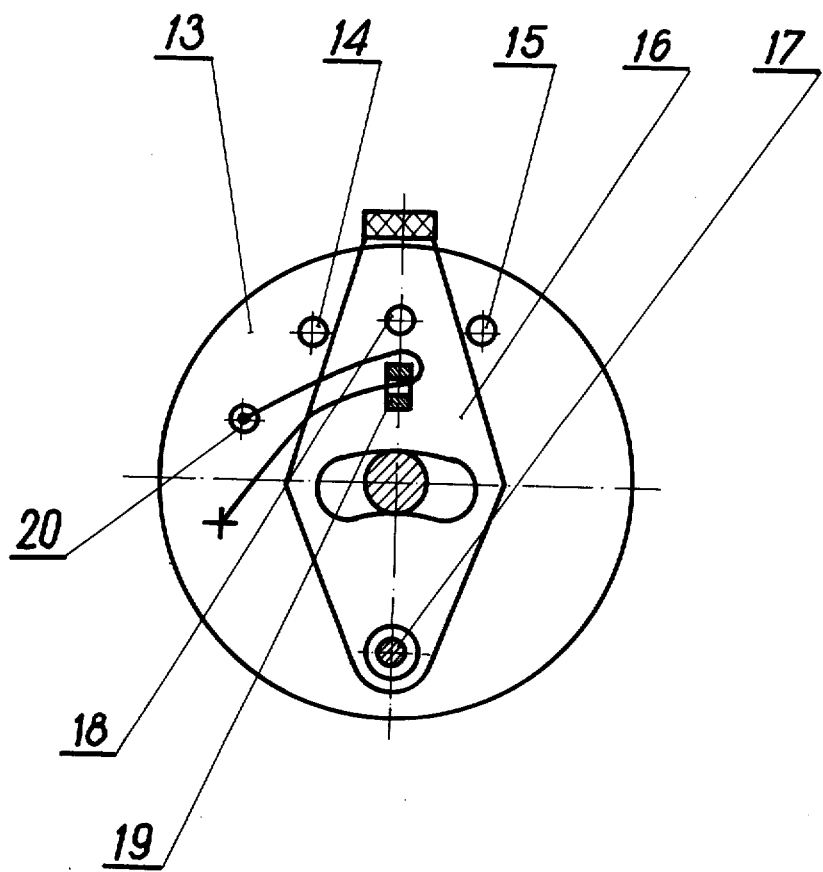
FIG. 8 is a front view of a shortening mechanism of an elbow mechanism control cable.

On the supporting rod 10 of the skeleton mounted in the forearm part 1 of an elbow, between the elbow mechanism and wrist joint there can be located a stationary cable shortening mechanism as shown in FIG. 8. This mechanism consists of disc 13 fixed on supporting rod 10 of the skeleton. On the disc 13 there is located lever 16 mounted for rotation on journal 17. Lever 16 is made in the form of a flat spring with center opening, the edges of which are in contact with the rod 10 of the skeleton and consequently restrict the movement of the lever 16. The end of lever 16 protrudes beyond the circumference of the disc 13 and forms a grip for operating the mechanism. In disc 13 there is hole 18 cooperating with the journals 14 and 15. On the lever there is also catch 19 with an eyelet. Cable 8 passes through hole 20 in disc 13 on the side of lever 16 and after having been passed through the eyelet in catch 19 is attached to disc 13.

The elbow mechanism according to the present invention operates as follows: The movement of the control harness for the artificial elbow causes tensioning of control cable 8, which pulls lock 5 from the disc of the arm part 1 of the mechanism via pulleys 4 and 6, thus causing in effect the unlocking of the mechanism. Further tensioning of cable 8 causes flexion of the elbow mechanism. In order to extend the elbow it is necessary to slightly release cable 8 by moving the control harness in the opposite direction. Cable 8 should always be slightly tensioned during the extending of the elbow and due to this, lock 5 is maintained in the unlocked postition. This is achieved by slowly releasing tension in control cable 8.

In order to lock the mechanism in the desired flexion position the tension of cable 8 is rapidly released. This causes, in effect; a simultaneous beginning of the elbow straightening motion and locking motion. However, mechanical inertia of the forearm during the forearm rotation, that is elbow extension, is considerably greater than the inertia of the lock during the locking motion and consequently at first the lock is being displaced from the locking position and at the same time the elbow mechanism has been only slightly extended.

The mechanism for shortening control cable 8 is intended to facilitate operation for the patient of the elbow in the upper range of the motion, this being particularly important when working with the prosthesis in seating position. In the postion corresponding to the maximum length of cable 8, journal 14 is located in hole 18 of lever 16. In order to shorten the cable it is necessary to pull spring lever 16 and set it in the opposite extreme position so that journal 15 can be introduced into hole 18.

Figure 9:
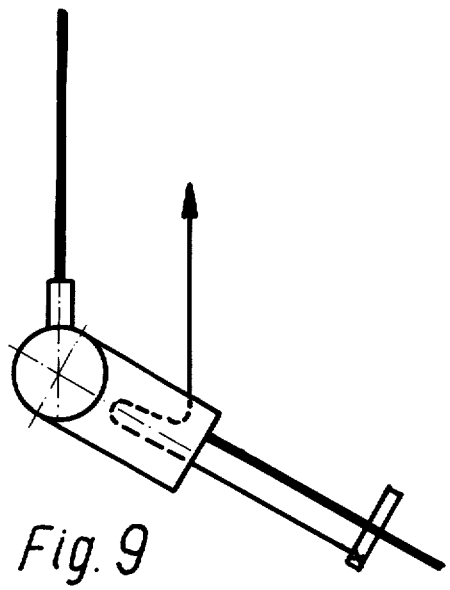
FIG. 9 is an illustration showing cooperation of the elbow mechanism and cable shortening mechanism in the case of a body-powered arm prosthesis.

FIG. 9 shows the cooperation of the elbow mechanism and the cable shortening mechanism in the case of a body powered prosthesis. In this case, the cable shortening mechanism facilitates operation of the elbow in the upper range of the elbow flexion. In the system presented in the figure the lower end of cable 8 is immovable and the upper end is connected with the control suspension of the artificial limb.

Figure 10:
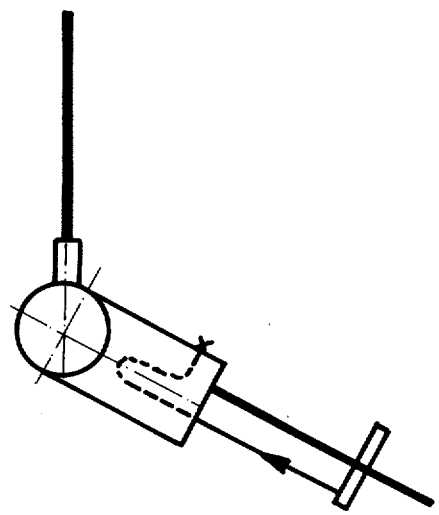
FIG. 10 illustrates such cooperation in the case of a cosmetic arm.

FIG. 10 shows the cooperation of the elbow mechanism and the cable shortening mechanism in a cosmetic limb with passive locking of the elbow mechanism. In the system presented in the figure the upper end of cable 8 is terminated with a knot hooked into the body of the elbow whereas the lower end of cable 8 is displaced in the cable shortening mechanism.

There will now be obvious to those skilled in the art many modifications and variations of the arrangements and mechanisms described hereinabove. These modifications and variations will not depart from the scope of the invention if defined by the following claims.

We claim:

1. Artificial elbow mechanism comprising an arm part including cut-out portions, a forearm part containing a first and a second pulley, said forearm part being rotatably connected to said arm part, a control cable, a locking mechanism operatively associated with said cut-out portions and being operated by said cable, said second pulley being located on said locking mechanism, said locking mechanism being located in said forearm part and being attached to said control cable in such a way that said control cable passes on said first pulley in the forearm part creating the point of application of forearm flexion force and then on said second pulley on said locking mechanism creating the point of application of a force for pulling out said locking mechanism from said cut-out in said arm part.

2. Artificial elbow mechanism as claimed in claim 1 comprising a supporting rod secured to said forearm part and a cable shortening mechanism including a disc with a plurality of journals thereon, said disc being fixed to said supporting rod in a plane perpendicular thereto, a revolving lever mounted on said disc and in the shape of a flat spring, said lever having a catch with an eyelet situated thereon and an opening provided in said lever of a diameter corresponding to the diameter of said journals, and wherein the control cable protrudes from the forearm part and passes through said opening in said disc and then through said eyelet in said catch situated on said lever and finally is attached to said disc.

3. Artificial elbow mechanism as claimed in claim 1 comprising a connecting link on said arm part, said connecting link including a cylindrical portion with a bore therein.

4. Artificial elbow mechanism as claimed in claim 1 comprising a revolvable attachment disc on said arm part for attachment with a stump.

5. Artificial elbow mechanism as claimed in claim 1 comprising a fixed mounting plate on said arm part for direct attachment in a stump socket.

6. Artificial elbow mechanism as claimed in claim 1 wherein said control cable projects externally from said artificial elbow mechanism beyond said second pulley whereby the control cable is capable of attachment with a further mechanism.

* * * * *